United States Patent
Müller et al.

[11] Patent Number: 6,083,946
[45] Date of Patent: *Jul. 4, 2000

[54] FUNGICIDE MIXTURES

[75] Inventors: Bernd Müller, Frankenthal; Hubert Sauter, Mannheim; Eberhard Ammermann, Heppenheim; Gisela Lorenz, Hambach; Siegfried Strathmann, Limburgerhof; Klaus Schelberger, Gönnheim; Maria Scherer, Landau; Dietrich Mappes, Westheim; Herbert Bayer, Mannheim; Ruth Müller, Friedelsheim, all of Germany

[73] Assignee: BASF Aktiengesellschaft, Ludwigshafen, Germany

[*] Notice: This patent is subject to a terminal disclaimer.

[21] Appl. No.: 09/171,601
[22] PCT Filed: Apr. 23, 1997
[86] PCT No.: PCT/EP97/02044
§ 371 Date: Oct. 22, 1998
§ 102(e) Date: Oct. 22, 1998
[87] PCT Pub. No.: WO97/40676
PCT Pub. Date: Nov. 6, 1997

[30] Foreign Application Priority Data

Apr. 26, 1996 [DE] Germany .............. 196 16 688
Apr. 26, 1996 [DE] Germany .............. 196 16 681
Sep. 2, 1996 [DE] Germany .............. 196 35 504

[51] Int. Cl.[7] .............. A01N 32/18; A01N 43/54; A01N 43/56; A01N 43/58; A01N 43/64
[52] U.S. Cl. .............. 514/247; 514/259; 514/383; 514/406; 514/407; 514/508; 514/538; 514/618; 514/619
[58] Field of Search ................ 514/247, 407, 514/383, 259, 406, 508, 538, 618, 619

[56] References Cited
FOREIGN PATENT DOCUMENTS 0289 879  11/1988  European Pat. Off. .
0326 329   8/1989  European Pat. Off. .

(List continued on next page.)

OTHER PUBLICATIONS

Bio. Soc. Trans. vol. 22, Jewess, 1994.

(List continued on next page.)

*Primary Examiner*—Allen J. Robinson
*Attorney, Agent, or Firm*—Keil & Weinkauf

[57] ABSTRACT

Fungicidal mixtures, comprising
a) a carbamate of the formula I

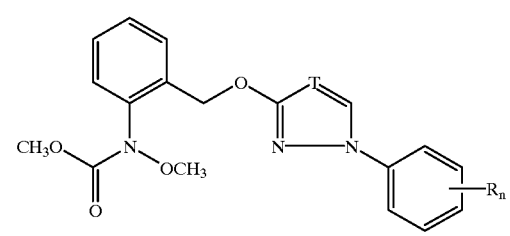

where T is CH or N, n is 0, 1 or 2 and R is halogen, $C_1$–$C_4$-alkyl or $C_1$–$C_4$-haloalkyl, it being possible for the radicals R to be different when n is 2, and/or b) an oxime ether of the formula II

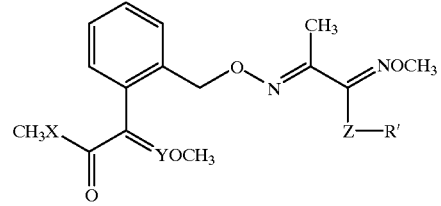

where the substituents have the following meaning:

X is oxygen or amino (NH);

Y is CH or N;

Z is oxygen, sulfur, amino (NH) or $C_1$–$C_4$-alkylamino (N—$C_1$–$C_4$-alkyl);

R' is $C_1$–$C_6$-alkyl, $C_1$–$C_6$-haloalkyl, $C_3$–$C_6$-alkenyl, $C_2$–$C_6$-haloalkenyl, $C_3$–$C_6$-alkynyl, $C_3$–$C_6$-haloalkynyl, $C_3$–$C_6$-cycloalkylmethyl, or is benzyl which can be partially or fully halogenated and/or have attached to it one to three of the following radicals: cyano, $C_1$–$C_4$-alkyl, $C_1$–$C_4$-haloalkyl, $C_1$–$C_4$-alkoxy, $C_1$–$C_4$-haloalkoxy, and $C_1$–$C_4$-alkylthio; and c) an acaricide selected from the group of the compounds III.a to III.d

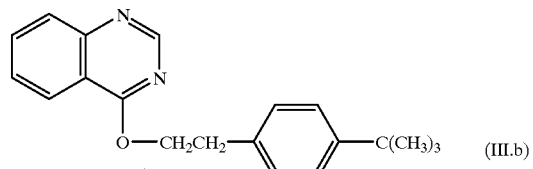

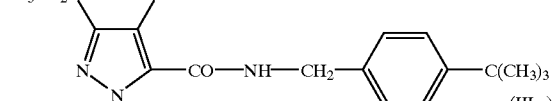

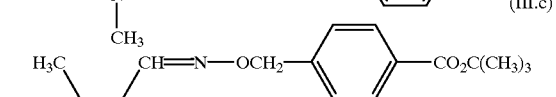

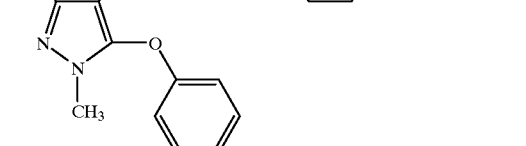

in a synergistically active amount.

22 Claims, No Drawings

FOREIGN PATENT DOCUMENTS

| | | |
|---|---|---|
| 19528 651 | 2/1997 | Germany . |
| 95/21153 | 8/1995 | WIPO . |
| 95/21154 | 8/1995 | WIPO . |
| 96/01256 | 1/1996 | WIPO . |
| 96/01258 | 1/1996 | WIPO . |
| 97/11606 | 4/1997 | WIPO |

OTHER PUBLICATIONS

Derwent Abst. JP 08198719.

Mitt. Biol. Bundesant, 1994, No. 301, 411.

FUNGICIDE MIXTURES

This application is a 371 of PCT/EP97/02044, filed Apr. 23, 1997.

The present invention relates to a fungicidal mixture which comprises a) a carbamate of the formula I

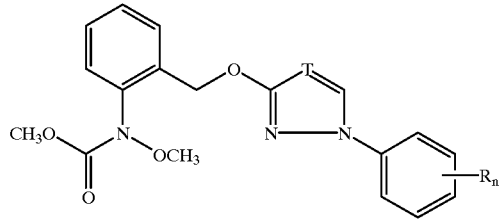

where T is CH or N, n is 0, 1 or 2 and R is halogen, $C_1$–$C_4$-alkyl or $C_1$–$C_4$-haloalkyl, it being possible for the radicals R to be different when n is 2, and/or b) an oxime ether of the formula II

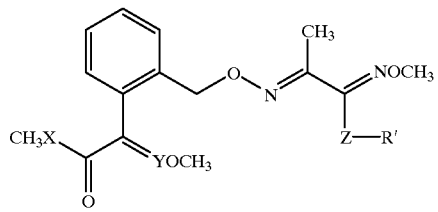

where the substituents have the following meaning:

X is oxygen or amino (NH);

Y is CH or N;

Z is oxygen, sulfur, amino (NH) or $C_1$–$C_4$-alkylamino (N—$C_1$–$C_4$-alkyl);

R' is $C_1$–$C_6$-alkyl, $C_1$–$C_6$-haloalkyl, $C_3$–$C_6$-alkenyl, $C_2$–$C_6$-haloalkenyl, $C_3$–$C_6$-alkynyl, $C_3$–$C_6$-haloalkynyl, $C_3$–$C_6$-cycloalkylmethyl, or is benzyl which can be partially or fully halogenated and/or have attached to it one to three of the following radicals: cyano, $C_1$–$C_4$-alkyl, $C_1$–$C_4$-haloalkyl, $C_1$–$C_4$-alkoxy, $C_1$–$C_4$-haloalkoxy, and $C_1$–$C_4$-alkylthio; and c) an acaricide selected from the group of the compounds III.a to III.d

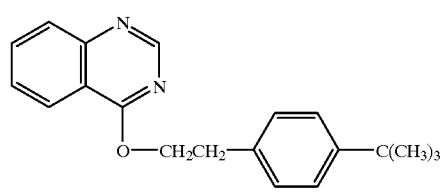

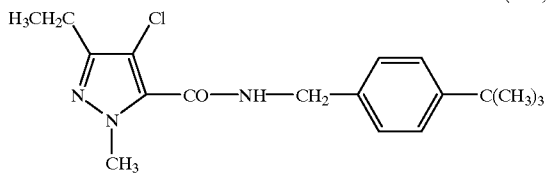

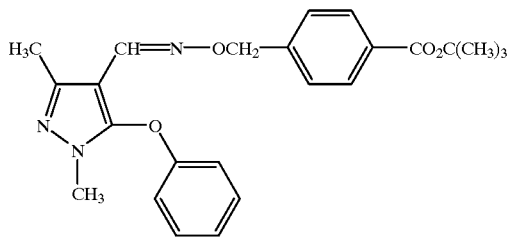

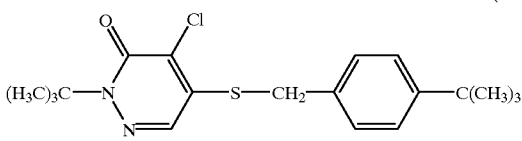

in a synergistically active amount.

Moreover, the invention relates to methods of controlling harmful fungi with mixtures of the compounds I and/or II and III and to the use of the compound I and/or II and the compounds III for the preparation of such mixtures.

The compounds of the formula I, their preparation and their action against harmful fungi have been disclosed in the literature (WO-A 96/01,256 and WO-A 96/01,258).

The compounds of the formula II, their preparation and their action against harmful fungi have been described in WO-A 95/21,153, WO-A 95/21,154 and DE-A 1 95 28 651.0.

The acaricides III, their preparation and their use against arachnids have also been disclosed (III.a: CAS RN 120928-09-8, common name: fenazaquin; III.b: EP-A 289 879, common name: tebufenpyrad; III.c: CAS RN 111812-58-9, common name: fenpyroximate; III.d: CAS RN 96489-71-3, common name: pyridaben).

It was an object of the present invention to provide mixtures which have an improved activity gainst harmful fungi combined with a reduced total amount of active ingredients applied (synergistic mixtures) with a view to reducing the rates of application and to improving the spectrum of action of the known compounds.

Accordingly, we have found that this object is achieved by the mixtures defined at the outset. Moreover, we have found that better control of the harmful fungi is possible by applying a compound I and/or II and the compounds III simultaneously together or separately or by applying a compound I and/or II and the compounds III in succession than when the individual compounds are used.

In particular, the formula I represents carbamates in which the combination of the substituents corresponds to one line of the table which follows:

| No. | T | $R_n$ |
|---|---|---|
| I.1 | N | 2-F |
| I.2 | N | 3-F |
| I.3 | N | 4-F |
| I.4 | N | 2-Cl |
| I.5 | N | 3-Cl |
| I.6 | N | 4-Cl |
| I.7 | N | 2-Br |
| I.8 | N | 3-Br |
| I.9 | N | 4-Br |
| I.10 | N | 2-$CH_3$ |
| I.11 | N | 3-$CH_3$ |
| I.12 | N | 4-$CH_3$ |
| I.13 | N | 2-$CH_2CH_3$ |
| I.14 | N | 3-$CH_2CH_3$ |
| I.15 | N | 4-$CH_2CH_3$ |
| I.16 | N | 2-$CH(CH_3)_2$ |
| I.17 | N | 3-$CH(CH_3)_2$ |
| I.18 | N | 4-$CH(CH_3)_2$ |
| I.19 | N | 2-$CF_3$ |
| I.20 | N | 3-$CF_3$ |
| I.21 | N | 4-$CF_3$ |
| I.22 | N | 2,4-$F_2$ |
| I.23 | N | 2,4-$Cl_2$ |
| I.24 | N | 3,4-$Cl_2$ |
| I.25 | N | 2-Cl, 4-$CH_3$ |
| I.26 | N | 3-Cl, 4-$CH_3$ |
| I.27 | CH | 2-F |
| I.28 | CH | 3-F |
| I.29 | CH | 4-F |
| I.30 | CH | 2-Cl |
| I.31 | CH | 3-Cl |
| I.32 | CH | 4-Cl |
| I.33 | CH | 2-Br |
| I.34 | CH | 3-Br |
| I.35 | CH | 4-Br |
| I.36 | CH | 2-$CH_3$ |
| I.37 | CH | 3-$CH_3$ |
| I.38 | CH | 4-$CH_3$ |
| I.39 | CH | 2-$CH_2CH_3$ |
| I.40 | CH | 3-$CH_2CH_3$ |
| I.41 | CH | 4-$CH_2CH_3$ |
| I.42 | CH | 2-$CH(CH_3)_2$ |
| I.43 | CH | 3-$CH(CH_3)_2$ |
| I.44 | CH | 4-$CH(CH_3)_2$ |
| I.45 | CH | 2-$CF_3$ |
| I.46 | CH | 3-$CF_3$ |
| I.47 | CH | 4-$CF_3$ |
| I.48 | CH | 2,4-$F_2$ |
| I.49 | CH | 2,4-$Cl_2$ |
| I.50 | CH | 3,4-$Cl_2$ |
| I.51 | CH | 2-Cl, 4-$CH_3$ |
| I.52 | CH | 3-Cl, 4-$CH_3$ |

The compounds I.12, I.23, I.32 and I.38 are especially preferred.

The formula II represents, in particular, oxime ethers where X is oxygen and Y is CH or X is amino and Y is N.

Also preferred are compounds I where Z is oxygen.

Equally preferred are compounds II where R' is alkyl or benzyl.

Particularly preferred with a view to their use in the synergistic mixtures according to the invention are the compounds I compiled in the tables which follow.

Table 2.

Compounds of the formula IIA, where ZR' for each compound corresponds to one line of Table A

TABLE 2

Compounds of the formula IIA, where ZR' for each compound corresponds to one line of Table A

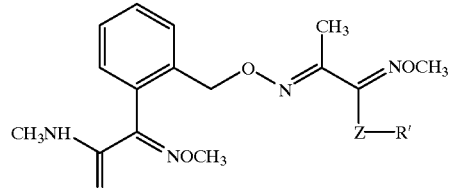

(IIA)

Table 3.

Compounds of the formula IIB, where ZR' for each compound corresponds to one line of Table A

TABLE 3

Compounds of the formula IIB, where ZR' for each compound corresponds to one line of Table A

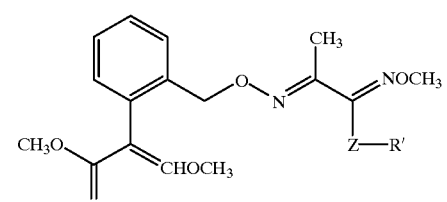

(IIB)

TABLE A

| No. | ZR' |
|---|---|
| II.1 | O—$CH_2CH_2CH_3$ |
| II.2 | O—$CH(CH_3)_2$ |
| II.3 | O—$CH_2CH_2CH_2CH_3$ |
| II.4 | O—$CH(CH_3)CH_2CH_3$ |
| II.5 | O—$CH_2CH(CH_3)_2$ |
| II.6 | O—$C(CH_3)_3$ |
| II.7 | S—$C(CH_3)_3$ |
| II.8 | O—CH($CH_3$)$CH_2CH_2CH_3$ |
| II.9 | O—$CH_2C(CH_3)_3$ |
| II.10 | O—$CH_2C(Cl)$=$CCl_2$ |
| II.11 | O—$CH_2CH$=CH—Cl(trans) |
| II.12 | O—$CH_2C(CH_3)$=$CH_2$ |
| II.13 | O—$CH_2$-(cyclopropyl) |
| II.14 | O—$CH_2$—$C_6H_5$ |
| II.15 | O—$CH_2$—[4-F—$C_6H_4$] |
| II.16 | O—$CH_2CH_3$ |
| II.17 | O—$CH(CH_2CH_3)_2$ |

Relative to the C=Y double bond, the compounds of the formula II can exist in the E or the Z configuration (relative to the carboxylic acid function). Accordingly, they can be used in the mixture according to the invention in each case either as the pure E or Z isomers or as an E/Z isomer mixture. Preferred is in each case the E/Z isomer mixture or the E isomer, the E isomer of the compound II being especially preferred.

The C=N double bonds of the oxime ether groups in the side chain of the compounds II can exist in each case as pure E or Z isomers or as E/Z isomer mixtures. The compounds II can be used in the mixtures according to the invention both as isomer mixtures and as pure isomers. Preferred with a view to their use are, in particular, compounds II where the terminal oxime ether group in the side chain is in the cis configuration (OCH$_3$ group to ZR').

Due to their basic character, the compounds I and II are capable of forming adducts or salts with inorganic or organic acids or with metal ions.

Examples of inorganic acids are hydrohalic acids such as hydrofluoric acid, hydrochloric acid, hydrobromic acid and hydroiodic acid, sulfuric acid, phosphoric acid and nitric acid.

Suitable organic acids are, for example, formic acid, carbonic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals having from 1 to 20 carbon atoms), arylsulfonic acids or -disulfonic acids (aromatic radicals such as phenyl and naphthyl which have attached to them one or two sulfo groups), alkylphosphonic acids (phosphonic acids having straight-chain or branched alkyl radicals of from 1 to 20 carbon atoms), arylphosphonic acids or -diphosphonic acids (aromatic radicals such as phenyl and naphthyl which have attached to them one or two phosphoric acid radicals), it being possible for the alkyl or aryl radicals to have attached to them further substituents, eg. p-toluenesulfonic acid, salicylic acid, p-aminosalicylic acid, 2-phenoxybenzoic acid, 2-acetoxybenzoic acid etc.

Suitable metal ions are, in particular, the ions of the elements of the second main group, in particular calcium and magnesium, and of the third and fourth main group, in particular aluminum, tin and lead, and of the first to eighth sub-group, in particular chromium, manganese, iron, cobalt, nickel, copper, zinc and others. Especially preferred are the metal ions of the elements of the sub-groups of the fourth period. The metals can in this case be in the various valences which they can assume.

When preparing the mixtures, it is preferred to employ the pure active ingredients I and/or II and III, with which further active ingredients against harmful fungi or other pests such as insects, arachnids or nematodes, or else herbicidal or growth-regulating active ingredients or fertilizers can be admixed, if so desired.

The mixtures of the compounds I and/or II and III, or the simultaneous joint or separate use of the compounds I and/or II and III, are distinguished by an outstanding activity against a broad spectrum of phytopathogenic fungi, in particular from the classes of the Ascomycetes, Deuteromycetes, Phycomycetes and Basidiomycetes. Some of them act systemically and can therefore be employed as foliar- and soil-acting fungicides.

They are especially important for controlling a large number of fungi in a variety of crop plants such as cotton, vegetable species (eg. cucumbers, beans and curcubits), barley, grass, oats, coffee, maize, fruit species, rice, rye, soybeans, grapevine, wheat, ornamentals, sugar cane, and a variety of seeds.

They are particularly suitable for controlling the following phytopathogenic fungi: Erysiphe graminis (powdery mildew) on cereals, Erysiphe cichoracearum and Sphaerotheca fuliginea on curcubits, Podosphaera leucotricha on apples, Puccinia species on cereals, Rhizoctonia species on cotton, rice and lawn, Ustilago species on cereals and sugar cane, Venturia inaequalis (scab) on apples, Helminthosporium species on cereals, Septoria nodorum on wheat, Botrytis cinerea (gray mold) on strawberries, vegetables, ornamentals and grapevines, Cercospora arachidicola on peanuts, Pseudocercosporella herpotrichoides on wheat and barley, Pyricularia oryzae on rice, Phytophthora infestans on potatoes and tomatoes, Pseudoperonospora species on cucurbits and hops, Plasmopara viticola on grapevines, Pseudoperonospora species on cucurbits and hops, Alternaria species on vegetables and fruit, and Fusarium and Verticillium species.

Furthermore, they can be used in the protection of materials (eg. in the protection of wood), for example against Paecilomyces variotii.

The compounds I and/or II and III can be applied simultaneously together or separately or in succession, the sequence, in the case of separate application, generally not having any effect on the result of the control measures.

The compounds I and III or II and III are normally used in a weight ratio of from 200:1 to 0.1:1, preferably 100:1 to 1:1, in particular 50:1 to 5:1 (III:I or III:II).

In the case of the compounds I and/or II, the application rates of the mixtures according to the invention are in general from 0.005 to 0.5 kg/ha, preferably 0.01 to 0.5 kg/ha, in particular 0.01 to 0.3 kg/ha, depending on the nature of the desired effect.

Correspondingly, in the case of the compounds III, the application rates are normally from 0.1 to 10 kg/ha, preferably 0.5 to 5 kg/ha, in particular 1 to 4 kg/ha.

For seed treatment, the application rates of the mixture used are generally from 0.001 to 100 g/kg seed, preferably 0.01 to 50 g/kg, in particular 0.01 to 10 g/kg.

If phytopathogenic harmful fungi are to be controlled, the separate or joint application of the compounds I and/or II and III or of the mixtures of the compounds I and/or II and III is effected by spraying or dusting the seeds, the plants or the soils before or after sowing of the plants, or before or after plant emergence.

The fungicidal synergistic mixtures according to the invention, or the compounds I and/or II and III, can be formulated for example in the form of ready-to-spray solutions, powders and suspensions or in the form of highly concentrated aqueous, oily or other suspensions, dispersions, emulsions, oil dispersions, pastes, dusts, materials for spreading or granules, and applied by spraying, atomizing, dusting, spreading or pouring. The use form depends on the intended purpose; in any case, it should guarantee as fine and uniform as possible a distribution of the mixture according to the invention.

The formulations are prepared in a manner known per se, eg. by adding solvents and/or carriers. It is usual to admix inert additives, such as emulsifiers or dispersants, with the formulations.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, of alkyl- and alkylarylsulfonates, of alkyl, lauryl ether and fatty alcohol sulfates, and salts of sulfated hexa-, hepta- and octadecanols or fatty alcohol glycol ethers, condensates of sulfonated naphthalene and its derivatives with formaldehyde, condensates of naphthalene, or of the naphthalenesulfonic acids, with phenol and formaldehyde, polyoxyethylene octylphenyl ether, ethoxylated isooctyl-, octyl- or nonylphenol, alkylphenol polyglycol ethers or tributylphenyl polyglycol ether, alkylaryl polyether alcohols, isotridecyl alcohol, fatty alcohol/ethylene oxide condensates, ethoxylated castor oil, polyoxyethylene or polyoxypropylene alkyl ethers, or lauryl alcohol polyglycol ether acetate, sorbitol esters, ligninsulfite waste liquors or methylcellulose.

Powders, materials for spreading and dusts can be prepared by mixing or jointly grinding the compounds I and/or II or III or the mixture of the compounds I and/or II and III with a solid carrier.

Granules (eg. coated granules, impregnated granules or homogeneous granules) are normally prepared by binding the active ingredient, or active ingredients, to a solid carrier.

Fillers or solid carriers are, for example, mineral earths such as silica gel, silicas, silicates, talc, kaolin, limestone, lime, chalk, bole, loess, clay, dolomite, diatomaceous earth, calcium sulfate, magnesium sulfate, magnesium oxide, ground synthetic materials, and fertilizers such as ammonium sulfate, ammonium phosphate, ammonium nitrate, ureas, and products of vegetable origin such as cereal meal, tree bark meal, wood meal and nutshell meal, cellulose powders or other solid carriers.

The formulations generally comprise from 0.1 to 95% by weight, preferably 0.5 to 90% by weight, of one of the compounds I and/or II or III, or of the mixture of the compounds I and/or II and III. The active ingredients are employed in a purity of from 90% to 100%, preferably 95% to 100% (according to NMR spectrum or HPLC).

The compounds I and/or II or III, or the mixtures, or the corresponding formulations, are applied by treating the harmful fungi or the plants, seeds, soils, areas, materials or spaces to be kept free from them with a fungicidally active amount of the mixture, or of the compounds I and/or II and III in the case of separate application. Application can be effected before or after infection by the harmful fungi.

The fungicidal activity of the compounds and of the mixtures is demonstrated by the following experiments:

The active ingredients, separately or together, are formulated as a 10% emulsion in a mixture of 70% by weight of cyclohexanone, 20% by weight of Nekanil® LN (Lutensol® AP6, wetting agent having emulsifying and dispersing action based on ethoxylated alkylphenols) and 10% by weight of Emulphor® EL (Emulan® EL, emulsifier based on ethoxylated fatty alcohols) and diluted with water to give the desired concentration.

Evaluation is carried out by determining the infected leaf areas in percent. These percentages are converted into efficacies. The expected efficacies of the mixtures of the active ingredients are determined using Colby's formula [R. S. Colby, Weeds 15, 20–22 (1967)] and compared with the observed efficacies.

Colby's formula:

$$E = x + y - x \cdot y / 100$$

E expected efficacy, expressed in % of the untreated control, when using the mixture of the active ingredients A and B at concentrations of a and b x efficacy, expressed in % of the untreated control, when using active ingredient A at a concentration of a y efficacy, expressed in % of the untreated control, when using active ingredient B at a concentration of b The efficacy (W) is calculated as follows using Abbot's formula:

$$W = (1 - \alpha) \cdot 100 / \beta$$

α is the fungal infection of the treated plants in % and β is the fungal infection of the untreated (control) plants in %

An efficacy of 0 means that the infection level of the treated plants corresponds to that of the untreated control plants; an efficacy of 100 means that the treated plants are not infected.

EXAMPLES 1–14

Efficacy against Botrytis cinerea on peppers

After 4–5 leaves had developed properly, pepper seedlings cv. "Neusiedler Ideal Elite" were sprayed to run-off with an aqueous preparation of active ingredient made with a stock solution of 10% active ingredient, 63% cyclohexanone and 27% emulsifier. Next day, the treated plants were inoculated with a spore suspension of Botrytis cinerea containing $1.7 \times 10^6$ spores/ml in a 2% strong aqueous Biomalz solution. The test plants were subsequently placed in a controlled-environment cabinet at 22 to 24° C. at high atmospheric humidity. After 5 days, the extent of fungal infection on the leaves was determined visually in %.

The visually determined values for the percentage of diseased leaf area were converted into efficacies as % of the untreated control. An efficacy of 0 is the same disease level as in the untreated control, an efficacy of 100 is a disease level of 0%. The expected efficacies for combinations of active ingredients were determined using Colby's formula (Colby, S. R. (Calculating synergistic and antagonistic responses of herbicide combinations", Weeds, 15, p. 20–22, 1967) and compared with the observed efficacies.

TABLE 4

| Ex. Active ingredient | Concentration of active ingredient in the spray mixture in ppm | Efficacy in % of the untreated control |
|---|---|---|
| 1V Control (untreated) | (disease level 70%) | 0 |
| 2V Compound No. I.38 of Table 1 = A | 63 | 44 |
| 3V IIIa = fenazaquin | 125 | 86 |
|  | 63 | 79 |
| 4V IIIb = tebufenpyrad | 125 | 72 |
|  | 63 | 58 |
| 5V IIIc = fenpyroxymate | 125 | 0 |
|  | 63 | 0 |
| 6V IIId = pyridaben | 125 | 16 |
|  | 63 | 16 |

TABLE 5

| Ex. | Concentration of active ingredient in the spray mixture in ppm | observed efficacy | calculated efficacy* |
|---|---|---|---|
| 7 | 63 A + 63 IIIa | 99 | 88 |
| 8 | 63 A + 125 IIIa | 99 | 92 |
| 9 | 63 + 63 IIIb | 93 | 77 |
| 10 | 63 A + 125 IIIb | 100 | 84 |
| 11 | 63 A + 63 IIIc | 96 | 44 |
| 12 | 63 A + 125 IIIc | 98 | 44 |
| 13 | 63 A + 63 IIId | 99 | 53 |
| 14 | 63 A + 125 IIId | 99 | 53 |

*calculated using Colby's formula

EXAMPLES 15–35

Efficacy against Pyricularia oryzae (protective)

Leaves of rice seedlings cv. "Tai-Nong 67" in pots were sprayed to run-off with an aqueous preparation of active ingredient made with a stock solution of 10% active ingredient, 63% cyclohexanone and 27% emulsifier. Next day, the plants were inoculated with an aqueous spore suspension of Pyricularia oryzae. The test plants were subsequently placed for 6 days in controlled-environment cabinets at 22–24° C. and relative atmospheric humidity of 95–99%. The extent of the disease development on the leaves was then determined visually.

The visually determined values for the percentage of diseased leaf area were converted into efficacies as % of the untreated control. An efficacy of 0 is the same disease level as in the untreated control, an efficacy of 100 is a disease level of 0%. The expected efficacies for combinations of active ingredients were determined using Colby's formula (Colby, S. R. (Calculating synergistic and antagonistic responses of herbicide combinations", Weeds, 15, p. 20–22, 1967) and compared with the observed efficacies.

TABLE 6

| Ex. | Active ingredient | Concentration of active ingredient in the spray mixture in ppm | Efficacy in % of the untreated control |
|---|---|---|---|
| 15V | Control (untreated) | (disease level 86%) | 0 |
| 16V | Compound No. 1.38 from Table 1 = A | 63 | 65 |
|  |  | 31 | 65 |
|  |  | 16 | 65 |
| 17V | IIIa = fenazaquin | 125 | 7 |
|  |  | 63 | 7 |
| 18V | IIIb = tebufenpyrad | 125 | 53 |
|  |  | 63 | 0 |
| 19V | IIIc = fenpyroxymate | 125 | 7 |
|  |  | 63 | 0 |
| 20V | IIId = pyridaben | 125 | 7 |
|  |  | 63 | 0 |

TABLE 7

| Ex. | Concentration of active ingredient in the spray mixture in ppm | observed efficacy | calculated efficacy* |
|---|---|---|---|
| 21 | 63 A + 125 IIIa | 99 | 67 |
| 22 | 31 A + 125 IIIa | 99 | 67 |
| 23 | 16 A + 63 IIIa | 99 | 67 |
| 24 | 63 A + 63 IIIb | 99 | 65 |
| 25 | 63 A + 125 IIIb | 99 | 84 |
| 26 | 31 A + 125 IIIb | 97 | 84 |
| 27 | 16 A + 63 IIIb | 99 | 65 |
| 28 | 63 A + 63 IIIc | 94 | 65 |
| 29 | 63 A + 125 IIIc | 99 | 67 |
| 30 | 31 A + 125 IIIc | 97 | 67 |
| 31 | 16 A + 63 IIIc | 80 | 65 |
| 32 | 63 A + 63 IIId | 94 | 67 |
| 33 | 63 A + 125 IIId | 97 | 65 |
| 34 | 31 A + 125 IIId | 94 | 65 |
| 35 | 16 A + 63 IIId | 88 | 67 |

*calculated using Colby's formula

EXAMPLES 36–53

Efficacy against Botrytis cinerea on peppers

After 4–5 leaves had developed properly, pepper seedlings cv. "Neusiedler Ideal Elite" were sprayed to run-off with an aqueous preparation of active ingredient made with a stock solution of 10% active ingredient, 63% cyclohexanone and 27% emulsifier. Next day, the treated plants were inoculated with a spore suspension of Botrytis cinerea containing $1.7 \times 10^6$ spores/ml in a 2% strong aqueous Biomalz solution. The test plants were subsequently placed in a controlled-environment cabinet at 22 to 24° C. at high atmospheric humidity. After 5 days, the extent of fungal infection on the leaves was determined visually in %.

The visually determined values for the percentage of diseased leaf area were converted into efficacies as % of the untreated control. An efficacy of 0 is the same disease level as in the untreated control, an efficacy of 100 is a disease level of 0%. The expected efficacies for combinations of active ingredients were determined using Colby's formula (Colby, S. R. (Calculating synergistic and antagonistic responses of herbicide combinations", Weeds, 15, p. 20–22, 1967) and compared with the observed efficacies.

TABLE 8

| Ex. | Active ingredient | Concentration of active ingredient in the spray mixture in ppm | Efficacy in % of the untreated control |
|---|---|---|---|
| 36V | Control (untreated) | (disease level 70%) | 0 |
| 37V | B = Tab. 2A, No. 2 | 63 | 30 |
|  |  | 16 | 16 |
| 38V | C = Tab. 2A, No. 4 | 31 | 44 |
|  |  | 16 | 44 |
| 39V | IIIa = fenazaquin | 125 | 86 |
|  |  | 63 | 79 |
| 40V | IIIb = tebufenpyrad | 63 | 58 |
| 41V | IIIc = fenpyroxymate | 125 | 0 |
|  |  | 63 | 0 |
| 42V | IIId = pyridaben | 125 | 16 |
|  |  | 63 | 16 |

TABLE 9

| Ex. | Concentration of active ingredient in the spray mixture in ppm | observed efficacy | calculated efficacy* |
|---|---|---|---|
| 43 | 16 B + 63 IIIa | 98 | 82 |
| 44 | 63 B + 63 IIIa | 93 | 85 |
| 45 | 16 B + 63 IIIb | 80 | 65 |
| 46 | 63 B + 63 IIIb | 92 | 70 |
| 47 | 16 B + 63 IIIc | 44 | 16 |
| 48 | 63 B + 125 IIIc | 50 | 30 |
| 49 | 63 B + 125 IIId | 100 | 41 |
| 50 | 16 B + 63 IIId | 58 | 30 |
| 51 | 31 C + 125 IIIa | 100 | 92 |
| 52 | 16 C + 63 IIIa | 100 | 88 |
| 53 | 16 C + 63 IIIb | 93 | 77 |

*calculated using Colby's formula

EXAMPLES 54–74

Efficacy against Pyricularia oryzae (protective)

Leaves of rice seedlings cv. "Tai-Nong 67" in pots were sprayed to run-off with an aqueous preparation of active ingredient made with a stock solution of 10% active ingredient, 63% cyclohexanone and 27% emulsifier. Next day, the plants were inoculated with an aqueous spore suspension of Pyricularia oryzae. The test plants were subsequently placed for 6 days in controlled-environment cabinets at 22–24° C. and relative atmospheric humidity of 95–99%. The extent of the disease development on the leaves was then determined visually.

The visually determined values for the percentage of diseased leaf area were converted into efficacies as % of the untreated control. An efficacy of 0 is the same disease level as in the untreated control, an efficacy of 100 is a disease level of 0%. The expected efficacies for combinations of active ingredients were determined using Colby's formula (Colby, S. R. (Calculating synergistic and antagonistic responses of herbicide combinations", Weeds, 15, p. 20–22, 1967) and compared with the observed efficacies.

TABLE 10

| Ex. | Active ingredient | Concentration of active ingredient in the spray mixture in ppm | Efficacy in % of the untreated control |
|---|---|---|---|
| 54V | Control (untreated) | (disease level 86%) | 0 |
| 55V | B = Tab. 2A, No. 2 | 63 | 83 |
|  |  | 31 | 77 |
|  |  | 16 | 18 |
| 56V | C = Tab. 2A, No. 4 | 31 | 83 |
|  |  | 16 | 30 |
| 57V | IIIa = fenazaquin | 125 | 7 |
|  |  | 63 | 7 |
| 58V | IIIb = tebufenpyrad | 63 | 0 |
| 59V | IIIc = fenpyroxymate | 125 | 7 |
|  |  | 63 | 0 |
| 60V | IIId = pyridaben | 125 | 7 |
|  |  | 63 | 0 |

TABLE 11

| Ex. | Concentration of active ingredient in the spray mixture in ppm | observed efficacy | calculated efficacy* |
|---|---|---|---|
| 61 | 63 B + 125 IIIa | 99 | 84 |
| 62 | 31 B + 125 IIIa | 94 | 78 |
| 63 | 16 B + 63 IIIa | 77 | 24 |
| 64 | 63 B + 63 IIIb | 99 | 63 |
| 65 | 16 B + 63 IIIb | 77 | 18 |
| 66 | 31 B + 125 IIIc | 91 | 78 |
| 67 | 63 B + 63 IIIc | 97 | 83 |
| 68 | 16 B + 63 IIIc | 83 | 18 |
| 69 | 63 B + 125 IIId | 99 | 84 |
| 70 | 31 B + 125 IIId | 99 | 79 |
| 71 | 16 B + 63 IIId | 77 | 18 |
| 72 | 31 C + 125 IIIa | 100 | 84 |
| 73 | 16 C + 63 IIIa | 99 | 35 |
| 74 | 16 C + 63 IIIb | 88 | 30 |
| 75 | 31 C + 125 IIIc | 99 | 84 |
| 76 | 16 C + 63 IIIc | 88 | 30 |
| 77 | 31 C + 125 IIId | 98 | 83 |

TABLE 11-continued

| Ex. | Concentration of active ingredient in the spray mixture in ppm | observed efficacy | calculated efficacy* |
|---|---|---|---|
| 78 | 16 C + 63 IIId | 65 | 35 |

*calculated using Colby's formula

The results of experiments 1–78 reveal that the observed efficacy in all mixing ratios exceeds the efficacy precalculated using colby's formula.

We claim:

1. A fungicidal composition comprising a) a carbamate I

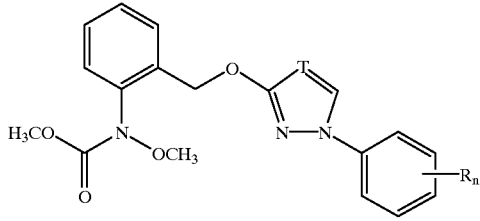
(I)

where T is CH or N, n is 0, 1 or 2 and R is halogen, $C_1$–$C_4$-alkyl or $C_1$–$C_4$-haloalkyl, it being possible for the radicals R to be different if n is 2, and c) an acaricide III selected from the group consisting of the compounds III.a to III.d

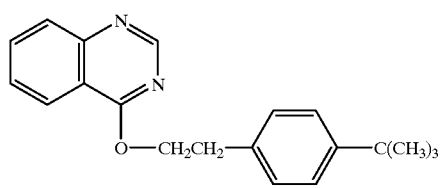
(III.a)

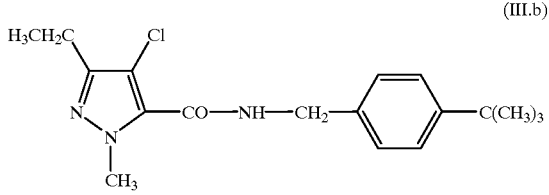
(III.b)

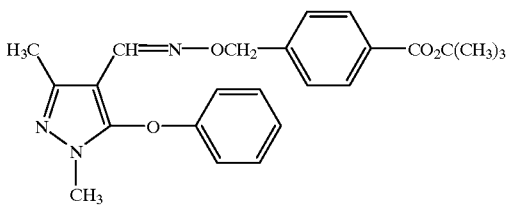
(III.c)

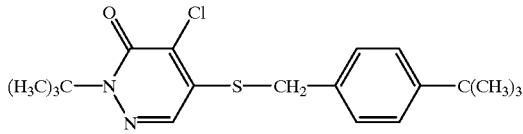
(III.d)

in a synergistically active amount.

2. The composition defined in claim 1 comprising the compound III.a.

3. The composition defined in claim 1 comprising the compound III.b.

4. The composition defined in claim 1 comprising the compound III.c.

5. The composition defined in claim 1 comprising the compound III.d.

6. The composition defined in claim 1, wherein the weight ratio of the acaricide III to the carbamate I is from 200:1 to 0.1:1.

7. The composition defined in claim 1, further comprising an oxime ether II

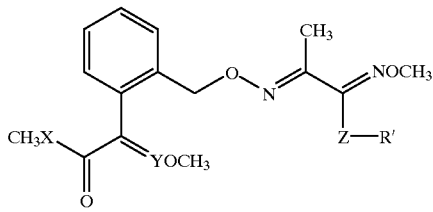
(II)

wherein the substituents have the following meaning:

X is oxygen or amino (NH);

Y is CH or N;

Z is oxygen, sulfur, amino (NH) or $C_1$–$C_4$-alkylamino (N-$C_1$–$C_4$-alkyl);

R' is $C_1$–$C_6$-alkyl, $C_1$–$C_6$-haloalkyl, $C_3$–$C_6$-alkenyl, $C_2$–$C_6$-haloalkenyl, $C_3$–$C_6$-alkynyl, $C_3$–$C_6$-haloalkynyl, $C_3$–$C_6$-cycloalkylmethyl, or benzyl which may be partially or fully halogenated and/or may carry one to three of the following radicals: cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio.

8. The composition defined in claim 7 comprising the compound III.a.

9. The composition defined in claim 7 comprising the compound III.b.

10. The composition defined in claim 7 comprising the compound III.c.

11. The composition defined in claim 7 comprising the compound III.d.

12. The composition defined in claim 7, wherein the weight ratio of the acaricide III to the carbamate I is from 200:1 to 0.1:1.

13. The composition defined in claim 7, wherein the weight ratio of the acaricide III to the oxime ether II is from 200:1 to 0.1:1.

14. A method for controlling harmful fungi, which comprises treating the harmful fungi, their environment, or the plants, seeds, soils, areas, materials or spaces to be kept free from said fungi with synergistically active amounts of a carbamate I and an acaricide III as set forth in claim 1.

15. The method defined in claim 14, wherein the carbamate I and the acaricide III are applied simultaneously together or separately or in succession.

16. The method defined in claim 14, wherein from 0.005 to 0.5 kg/ha of the carbamate I are applied.

17. The method defined in claim wherein from 0.1 to 10 kg/ha of the acaricide III are applied.

18. The method defined in claim 7, further comprising treating the harmful fungi, their environment, or the plants, seeds, soils, areas, materials or spaces to be kept free from said fungi with a synergistically effective amount of an oxime ether II

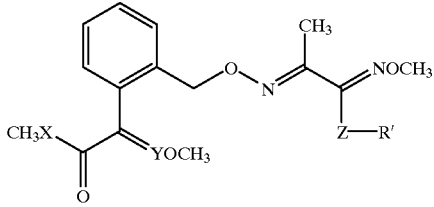
(I)

wherein the substituents have the following meaning:
X is oxygen or amino (NH);
Y is CH or N;
z is oxygen, sulfur, amino (NH) or $C_1$–$C_4$-alkylamino (N—$C_1$–$C_4$-alkyl);
R' is $C_1$–$C_6$-alkyl, $C_1$–$C_6$-haloalkyl, $C_3$–$C_6$-alkenyl, $C_2$–$C_6$-haloalkenyl, $C_3$–$C_6$-alkynyl, $C_3$–$C_6$-haloalkynyl, $C_3$–$C_6$-cycloalkylmethyl, or benzyl which may be partially or fully halogenated and/or may carry one to three of the following radicals: cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio.

19. The method defined in claim 18, wherein the carbamate I and the acaricide III are applied simultaneously together or separately or in succession.

20. The method defined in claim 18, wherein from 0.005 to 0.5 kg/ha of the carbamate I are applied.

21. The method defined in claim 18, wherein from 0.005 to 0.5 kg/ha of the oxime ether II are applied.

22. The method defined in claim 18, wherein from 0.1 to 10 kg/ha of the acaricide III are applied.

* * * * *

UNITED STATES PATENT AND TRADEMARK OFFICE
CERTIFICATE OF CORRECTION

PATENT NO.   : 6,083,946
DATED        : July 4, 2000
INVENTOR(S)  : Mueller et al.

It is certified that error appears in the above-identified patent and that said Letters Patent is hereby corrected as shown below:

Column 13, claim 1,
Line 40, "III.a" should be -- III.b --
Line 42, "III.a" and the corresponding structural formula should be deleted.
Line 60, formula (III.c) should read:

-- 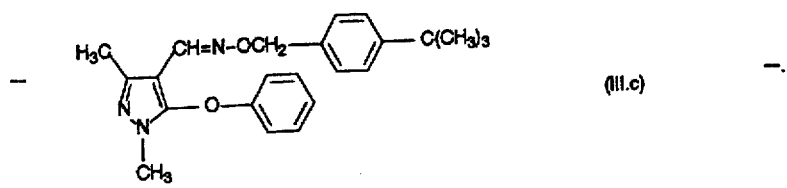 (III.c) --.

Cancel claims 2 and 8.

Column 15, claim 17,
Line 3, after "claim" insert -- 14 --.

Column 16, claim 18,
Line 2, "z" should be -- Z --.

Signed and Sealed this

Fifth Day of February, 2002

JAMES E. ROGAN
*Director of the United States Patent and Trademark Office*